(12) United States Patent
Holtwick et al.

(10) Patent No.: US 9,511,191 B2
(45) Date of Patent: Dec. 6, 2016

(54) MEDICAMENT GUIDING ASSEMBLY FOR A DRUG DELIVERY DEVICE

(71) Applicant: SANOFI-AVENTIS DEUTSCHLAND GMBH, Frankfurt am Main (DE)

(72) Inventors: Marc Holtwick, Frankfurt am Main (DE); Martin Haupt, Vienna (AT)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days.

(21) Appl. No.: 14/353,523

(22) PCT Filed: Nov. 15, 2012

(86) PCT No.: PCT/EP2012/072789
§ 371 (c)(1),
(2) Date: Apr. 23, 2014

(87) PCT Pub. No.: WO2013/072440
PCT Pub. Date: May 23, 2013

(65) Prior Publication Data
US 2014/0316341 A1 Oct. 23, 2014

(30) Foreign Application Priority Data
Nov. 16, 2011 (EP) .................................... 11189282

(51) Int. Cl.
*A61M 5/31* (2006.01)
*B29C 45/16* (2006.01)
(Continued)

(52) U.S. Cl.
CPC ................. *A61M 5/31* (2013.01); *A61M 5/20* (2013.01); *B29C 45/1671* (2013.01);
(Continued)

(58) Field of Classification Search
CPC ...... A61M 5/31; A61M 2207/00; A61M 5/20; A61M 5/24; A61M 5/19; A61M 2005/1787; A61M 2207/10
See application file for complete search history.

(56) References Cited

U.S. PATENT DOCUMENTS

| 4,105,162 A | 8/1978 | Drori | |
| 2005/0074340 A1* | 4/2005 | Xu et al. | 417/395 |

(Continued)

FOREIGN PATENT DOCUMENTS

| CN | 1275884 | 12/2000 |
| WO | 99/18771 | 4/1999 |
| WO | 2005/088710 | 9/2005 |

OTHER PUBLICATIONS

International Search Report for Int. App. No. PCT/EP2012/072789, completed Feb. 6, 2013.
(Continued)

*Primary Examiner* — Laura Bouchelle
*Assistant Examiner* — Melissa A Snyder
(74) *Attorney, Agent, or Firm* — McDonnell Boehnen Hulbert & Berghoff LLP

(57) ABSTRACT

A fluid guiding assembly for a drug delivery device is presented having a first member, a cover part adjacently disposed to the first member and being in non-bonded surface contact with a surface portion of the first member thereby forming an interface area, at least one channel structure extending along the interface area of first member and cover part and being formed by at least one recess in either the first member and/or in the cover part, and a second member being in contact with the cover part and being bonded to the first member by way of injection molding to fix the cover part relative to the first member.

14 Claims, 3 Drawing Sheets

(51) Int. Cl.
*A61M 5/20* (2006.01)
*A61M 5/14* (2006.01)
*A61M 5/24* (2006.01)
*A61M 5/19* (2006.01)
*A61M 5/178* (2006.01)

(52) U.S. Cl.
CPC ............... *A61M 5/141* (2013.01); *A61M 5/19* (2013.01); *A61M 5/24* (2013.01); *A61M 2005/1787* (2013.01); *A61M 2207/00* (2013.01)

(56) References Cited

U.S. PATENT DOCUMENTS

2005/0277882 A1* 12/2005 Kriesel .................. 604/131
2010/0318063 A1    12/2010 Soll

OTHER PUBLICATIONS

Webb D.P., et al., "Packaging of Microfluidic Devices for Fluid Interconnection Using Thermoplastics," Journal of Microelectromechanical Systems, IEE Service Center, US, vol. 18, No. 2, Apr. 1, 2009, pp. 354-362.

* cited by examiner

MEDICAMENT GUIDING ASSEMBLY FOR A DRUG DELIVERY DEVICE

CROSS REFERENCE TO RELATED APPLICATIONS

The present application is a U.S. National Phase Application pursuant to 35 U.S.C. §371 of International Application No. PCT/EP2012/072789 filed Nov. 15, 2012, which claims priority to European Patent Application No. 11189282.4 filed Nov. 16, 2011. The entire disclosure contents of these applications are herewith incorporated by reference into the present application.

TECHNICAL FIELD

The present invention relates to a fluid guiding assembly for a drug delivery device providing at least one fluid channel adapted to guide a fluid, e.g. a medicament. The invention further relates to a method of a manufacturing such a fluid guiding assembly.

BACKGROUND

Drug delivery devices for setting and dispensing a single or multiple doses of a liquid medicament are as such well-known in the art. Generally, such devices have substantially a similar purpose as that of an ordinary syringe.

Drug delivery devices, in particular pen-type injectors have to meet a number of user-specific requirements. For instance, with patient's suffering chronic diseases, such like diabetes, the patient may be physically infirm and may also have impaired vision. Suitable drug delivery devices especially intended for home medication therefore need to be robust in construction and should be easy to use. Furthermore, manipulation and general handling of the device and its components should be intelligible and easy understandable. Moreover, a dose setting as well as a dose dispensing procedure must be easy to operate and has to be unambiguous.

For instance, such devices comprise a housing to receive a cartridge being at least partially filled with the medicament to be dispensed. The device further comprises a drive mechanism, typically having a displaceable piston rod to operably engage with a piston of the cartridge. By means of the drive mechanism and its piston rod, the piston of the cartridge can be displaced in a distal or dispensing direction and may therefore expel a pre-defined amount of the medicament via a piercing assembly which is to be releasably coupled with a distal or dispensing end of the housing of the drug delivery device.

Depending on the type of medicament and the way the medicament has to be prepared prior to be administered to a patient, particular drug delivery devices have to provide a medicament guiding structure, e.g. downstream of a cartridge but upstream of a dispensing end. Manufacturing of such fluid guiding structures or fluid guiding channels is somewhat crucial. Especially when the fluid guiding structure is made of plastic, in particular of thermoplastic material, a desirable miniaturization of fluid guiding structures or channel structures is difficult to achieve. For instance by way of injection molding processes complicated or multiply wound hollow channel structures cannot be realized.

Especially with drug delivery devices and applications it would be of particular benefit to provide fluid guiding channels with a comparatively small cross section in order to minimize a dead volume of the fluid guiding structure for not unnecessarily wasting precious or expensive medicaments or the like substances to be guided therethrough.

Moreover, fluid guiding plastic components should be substantially inert or highly compatible to the medicament or substance to be guided therewith. Hence, the range of plastic components suitable for medicament guiding purposes is rather limited.

In general, small sized channel structures can be manufactured by providing a member featuring a channel-forming groove or recess extending across a surface portion. By covering the surface portion with a cover part and by bonding cover part and said member together, a closed fluid-guiding channel structure can be provided in principle. Bonding of the member and the cover part may be provided by way of laser welding or ultrasonic welding as well as by making use of adhesives. Such mutual bonding of member and cover part involves application of heat, which may eventually deteriorate the chemically inert properties of the respective plastic material.

Moreover, chemically inert plastic materials are rather unsuitable for e.g. laser welding due to insufficient light absorption properties. Enhancement of light absorption can in principle be attained by embedding light absorbing particles, such like soot particles, in the bulk of such plastic materials. However, this may further deteriorate the purity of the plastic material and pre-defined as well as required chemically inert properties may no longer be met.

Also, when bonding the member and the cover part together by means of an adhesive, a portion of the adhesive may intrude into the channel structure, thereby enhancing a risk, that the medicament flowing therethrough gets contaminated.

It is therefore one object of the present invention to provide a fluid guiding assembly for a drug delivery device which is easy to assemble and which provides a liquid-tight channel structure of pre-defined size and/or geometry without directly bonding together the channel forming parts. The invention therefore aims to provide an improved method of manufacturing a fluid guiding assembly without deteriorating the plastic component the channel structure is made from. Said method of manufacturing should be highly reproducible and should provide a long lasting liquid-tight fluid guiding channel structure in plastic-based parts of a fluid guiding assembly.

SUMMARY

In a first aspect, a fluid guiding assembly for a drug delivery device is provided comprising a first member and a cover part adjacently disposed to the member in a non-bonded contact configuration to a surface portion of said member. Hence, the cover part is loosely fitted or is kept in loose contact with the first member. The surface portions, in which first member and cover part get in direction contact with each other define an interface area of first member and cover part.

In order to provide at least one channel structure, first member and/or cover part comprise at least one recess, a cavity or a groove extending along the interface area of member and cover part. The recess can be formed in a surface portion of the member facing towards the cover part. Additionally or alternatively, a recess or groove can also be formed in a surface portion of the cover part facing towards the member. Also, first member and cover part may each comprise a groove or recess mutually complementing to form a closed channel structure when first member and cover part are assembled together.

The cover part and the first member are arranged in a direct abutment configuration, such that e.g. a recess or groove provided in a surface portion of the first member is tightly covered by a flat or recessed shaped cover part.

Since cover part and first member remain in non-bonded or non-interconnected contact configuration, the fluid guiding assembly comprises a second member being at least in contact with the cover part and being further engaged with the first member to positionally fix the cover part relative to the first member.

Furthermore, the second member is bonded to the first member by way of injection molding. This way, the second member is inherently bonded to the first member while it is manufactured. The material the second component is made of can therefore be substance-bonded to the first member without making use of any supplemental adhesive or other bonding or fastening means.

As a consequence, first and second member do not have to be assembled manually. A mutual assembly of first and second members takes place while the second member is produced and injection molded. The first member may therefore contribute and form a part of a mold adapted to form the second member. In effect, the surface of the first member to engage with the second member does not have to fulfill particular geometric specifications. The second member arbitrarily adapts even to varying shapes and geometries of the first member.

It may be of particular benefit, when the second member gets in contact with a surface portion of the cover part that faces away from the interface area of the first member and cover part. Moreover, the second member preferably extends across and beyond the cover part in order to firmly fix the cover part to the first member. The cover part may therefore be embraced by the second member.

Moreover, the cover part may be at least partially sandwiched and/or clamped between the first and the second member, which are directly bonded to each other.

It is particularly intended, that only first and second members are mutually interconnected in a material connecting way. In particular, the second member is at least partially injection molded over the first member and the cover part.

This way, the first member and the cover part do not have to be directly bonded or interconnected with each other. Consequently, the cover part and the first member at least in their interface area do not have to become subject to heat treatment or energy deposition for the purpose of bonding first and second parts together.

Hence, the first member and the cover part can remain indirectly fixed and interconnected via the second member. Even though first member and cover part are indirectly fixed to each other, they may be rather immobile with respect to each other. In particular, first member and cover part may be rigidly and firmly connected. Moreover, first member, second member and/or cover part may comprise a rather rigid and inflexible structure.

In a preferred aspect the first member comprises an injection molded plastic component. By way of injection molding, the first member can be inherently provided with a recess or groove extending along a particular surface portion thereof to at least partially form the channel structure which is to be closed by the cover part. The first member and/or the cover part preferably comprise a plastic material being substantially inert to substances to be led through the channel structure. The materials first member and cover member are made of should therefore be classified as biocompatible. Preferably the first member and/or the cover part comprise a plastic material being approved by the US Food and Drug Administration (FDA). Consequently, the plastic materials of choice meet the standards according to US government regulation (CFR) 21 and are classified as FDA compliant. Among FDA-compliant plastic materials first body part and/or cover part may comprise plastic materials such like Cyclo Olefin Polymers (COP).

In a further preferred aspect, also the second member comprises an injection molded plastic component bonded to the first member by way of injection molding. The second member may be also bonded to the cover part. Since the channel structure is exclusively formed and enclosed by the first member and the cover part, the second member does not necessarily have to be made of FDA-compliant material or of biocompatible plastic material. Hence, first and second members may comprise different plastic compositions.

In this context, it is of particular benefit, when the second member is bonded with at least the first member by way of injection molding. Hence the second member is inherently connected to the first member during such molding process.

The present invention particularly focuses but is not limited to an assembly injection process. The first member can for instance be provided by way of a first injection step. Opening of a respective mold may allow to assemble fluid manipulating components, such like back-flow valves into the channel structure. After that the cover part can be positioned on the pre-defined surface portion of the first member to form close the channel structure. Thereafter, without removing the first member from the mold, in a subsequent and second injection molding step, the second member can be formed by establishing a substance-to-substance bonding between first and second members.

In a further preferred aspect, first and second members are mutually interconnected in a region located outside the cover part. Consequently, first and second members comprise a somewhat mutually corresponding shape and geometry in order to sandwich the cover part therebetween.

In this context, it may be also of further benefit, when the second member and/or the first member at least partially enclose or partially surround the cover part. This may facilitate correct mutual assembly of first member and cover part. Hence, first member and cover part may comprise mutually corresponding positioning members in order to unequivocally arrange cover part and first member. Mutual interconnection and/or mutual bonding of first and second members may be based on an integral joint formed by respective surface portions of first member and second member that face towards each other.

It is also conceivable, that the second member not only encloses the cover part but also at least partially encloses the first member. Generally, the second member not only has to abut with a particular surface portion of the first member but the second member also may extends across lateral or outer side edges of the first member so as to embrace the first member and to establish a positive engagement between first and second members.

In still another aspect, the interface between cover part and first member is substantially liquid-tight. Hence, the cover part is to be assembled and/or pressed on the surface portion of the first member in such a way, that a channel formed in the interface area of first member and cover part does not leak when it becomes subject to respectable fluid pressure.

In a further preferred aspect, the fluid guiding assembly is designed as a needle hub or as a cartridge hub of a drug delivery device, which for instance provides administering of a medicament by way of injection. In other words, a needle and/or cartridge hub of a drug delivery device is provided comprising at least one fluid guiding assembly as described above. The guiding assembly may be of particular use with drug delivery devices, wherein two or more medicaments provided in different cartridges have to be combined or mixed prior or during delivery to a patient. Such a guiding assembly has further application in circumstances, wherein different medicaments provided by different containers or cartridges are to be dispensed in a sequential manner through a common single dispensing outlet of the drug delivery device. Hence, the guiding assembly may be used as a 2-in-1 junction member or as a T-piece guiding member. Typically, such fluid guiding assembly is to be arranged downstream of one or more medicament containing cartridge(s) of a drug delivery device but upstream of a dispensing end, which may be in fluid connection with a replaceable injection needle or other fluid guiding structures.

According to a further independent aspect the invention also relates to a drug delivery device adapted to dispense a pre-defined amount of at least one medicament via an outlet. The drug delivery device, which may be designed as a hand-held injector or as a pen-type injector comprises a housing to receive at least one cartridge being at least partially filled with a medicament. Moreover, the device comprises a dispensing end via which a pre-defined amount of the medicament is to be dispensed. Furthermore, the drug delivery device comprises a fluid guiding assembly as described above being disposed in a fluid path between the cartridge and the dispensing end, so that the at least one channel structure provided by the fluid guiding assembly can provide a respective fluid guiding functionality.

According to a further independent aspect, there is also provided a method of manufacturing a fluid guiding assembly as described above. In an initial step, a first member is provided, which may be produced by way of injection molding or which may be otherwise provided, e.g. by a supplier. Starting with the first member, in an optional step, fluid manipulating member, such like diaphragms and/or valves may be arranged in a recessed portion or in a groove of the first member. Thereafter in a second step, a cover part is arranged adjacent to the first member to form an interface area of first member and cover part. In the region of the interface area first member and cover part get in direct contact with each other. Moreover, the cover part and/or the first member comprise at least one recess extending along the interface area to form a channel structure applicable to guide a fluid, preferably to guide a medicament therethrough. Here, either one or both of the cover part and the first member may comprise a grooved or recessed structure to form or to complement a fluid guiding channel.

For instance, the injection molded first member features a recess extending along an upper surface and the cover part of substantially flat and even-shaped geometry is to be placed on top of said surface in order to close the recessed structure of the first member. Alternatively, it is also conceivable, that the cover part features a recess or groove at a surface facing towards the abutment surface of the first member, which in this case may be substantially flat or even shaped.

After having covered the recess in the interface area of first member and/or cover part, the first member is bonded with a second member by way of injection molding, thereby also getting in contact or in abutment with the cover part to fix the same relative to the first member. By mutually interconnecting first and second members and by arranging the cover part therebetween, the cover part can be positionally fixed relative to both, first and second members. By firmly bonding first and second members, a liquid-tight sealing contact between first member and cover part can be attained.

The second member is at least bonded, preferably it is integrally joined to the first member by way of a subsequent injection molding process after first member and cover part have been mutually assembled. Prior to mutual assembly of first member and cover part, optional valve elements or the like can be assembled in the recessed surface structure of first member and/or cover part. This way, an assembly injection process can be provided, wherein the first member may remain in a respective mold or part of a mold until the second member has been integrally joined thereto.

It is of particular benefit, when the first member and/or the cover part are injected molded and comprise at least one recess extending across an interface forming surface portion. As already mentioned above, it is of particular benefit when cover part and/or first member comprise or are made of an inert or biocompatible plastic material being of FDA-compliant type in view of medicament and drugs to be administered to a patient, e.g. by way of injection.

Moreover and according to another preferred aspect, the cover part is separately or individually pressed against the first member during or prior to injection molding of the second member. This way, a particularly sealed and liquid-tight mutual abutment and sealing configuration of cover part and first member can be attained. For the purpose of providing a respective sealing pressure, preload ejectors or pressure pieces may exert a respective pressure to the surface of the cover part which is located opposite the interface area. This way, the cover part can be firmly pressed against the first member in order to provide a sufficiently sealed channel structure between the first member and the cover part.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(02)25, Asp28] Exendin-4(1-39),
des Pro36 [Met(O)14 Trp(02)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the pertinent art that various modifications and variations can be made to the present invention without departing from the spirit and scope of the invention. Further, it is to be noted, that any reference signs used in the appended claims are not to be construed as limiting the scope of the present invention. Moreover, all features and embodiments as described herein are to be understood to equally apply to the fluid guiding assembly, to the drug delivery device as well as to the method to manufacture the fluid guiding assembly. In particular, a mentioning of a component being configured or arranged to conduct a particular operation is also to be understood to disclose a respective method step and vice versa.

BRIEF DESCRIPTION OF THE DRAWINGS

In the following, preferred embodiments among a manifold of optional and equally conceivable ways to carry out the invention will be described by making reference to the drawings, in which.

DETAILED DESCRIPTION

Figure 1:
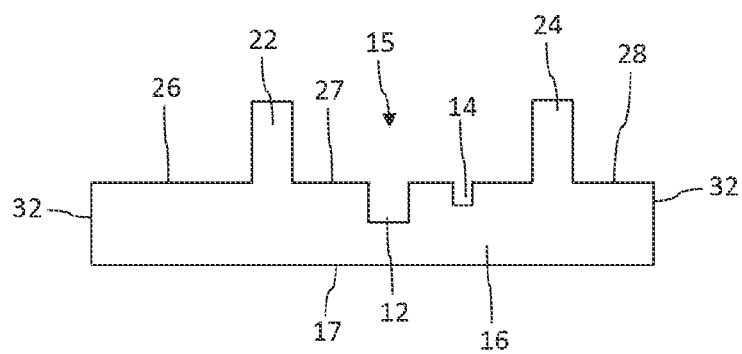
FIG. 1 schematically illustrates a side view of an injection molded first member of a fluid guiding assembly.
Figure 2:
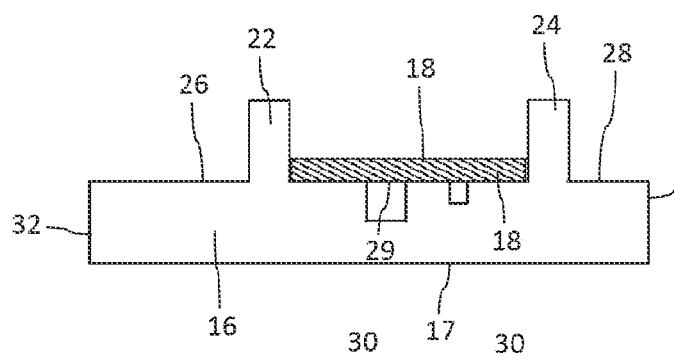
FIG. 2 shows the first member according to FIG. 1 with a cover part attached thereto.
Figure 3:
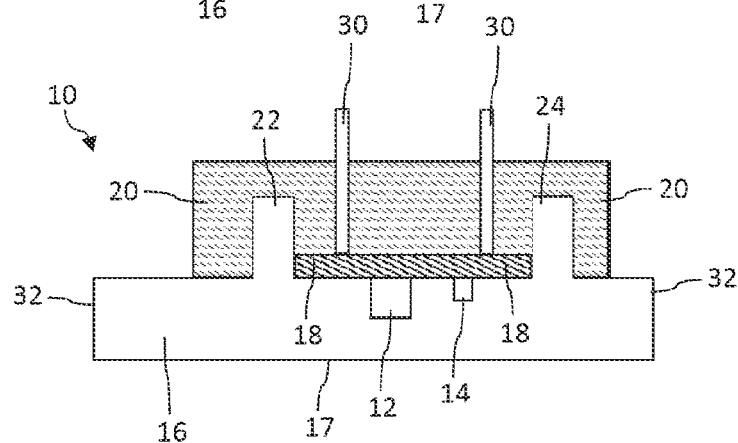
FIG. 3 shows a final stage of assembly of the fluid guiding assembly wherein a second member is integrally join with the first member to fix the cover part thereto.
Figure 4:
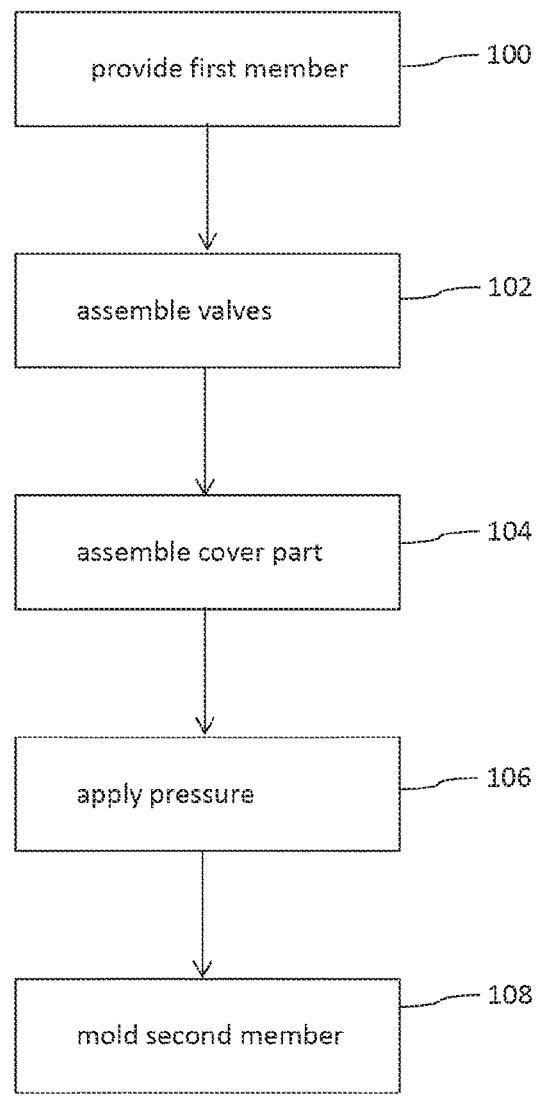
FIG. 4 is an example flowchart illustrating a method of manufacturing the fluid guiding assembly.

The sequence of FIGS. 1 to 3 shows sequential steps of manufacturing a fluid guiding assembly 10 featuring a small size flow through channel structure 12, 14. The diameter of the fluid channel 12, 14 may range between 0.01 mm and 10 mm. The diameter may particularly lie between 0.1 mm and 1 mm, for instance it is about 0.3 mm. A ratio between the length and the diameter of the fluid channels may range between 10:1 and 1000:1. In particular, the length:diameter ratio may range between 20:1 and 100:1. It may be around 33:1 or 66:1. In this context, the length of the fluid channel may correspond to the longest fluid communication path of the fluid channels of the fluid guiding assembly 10.

Assembly of the fluid guiding assembly 10 as shown in FIG. 3 starts with a first member 16 as illustrated in FIG. 1. The first member 16 may be manufactured or made of thermoplastic, preferably of FDA-compliant or biocompatible plastic material. As shown in FIG. 1, the first member 16 comprises two recesses 12, 14 extending along a substantially flat shaped upper surface portion 27 of the first member 16. The channel structures 12, 14 of required size can be manufactured by way of the injection molding process. However, those channels or grooves 12, 14 can also be subsequently etched or engraved. In a subsequent step of assembly, the upper surface portion 27 of the first member 16 is covered with a flat or even shaped cover part 18, thereby forming a closed channel structure 12, 14. The channels 12, 14 are only illustrated in cross section. They extend substantially perpendicular to the paper level.

Prior to arranging the cover part 18 on top of the first member 16 also valves, in particular back-flow valves may be optionally disposed in the recessed structure 12, 14.

The first member 16 also comprises two upwardly pointing projections 22, 24 defining an interface area 15 therebetween which matches with the lateral dimension of the cover part 18. This way, the cover part 18 to be arranged on top of the first member 16 can be preliminarily fixed in a non-bonded or loosened way. As indicated in FIG. 2, the cover part 18 is laterally fixed by oppositely located protrusions 22, 24 and under the effect of gravity pointing downwards in FIG. 2.

In order to provide a sufficient sealing of the fluid guiding channel structures 12, 14, the cover part 18 is pressed downwardly towards the first member 16 by means of two or more pressure pieces 30. Hence, first member 16 and cover part 18 are pressed together. Simultaneous to this pressure application, the pre-assembly of first member 16 and cover part 18 is subject to a subsequent injection molding step, by way of which a second member 20 is to be integrally joined with at least the first member 16. The second member 20 may also integrally join or adhesively bond to the upward facing surface of the cover part 18. However, in order to provide a sealing of the channels 12, 14 the second member 20 should exert a respective downward pointing holding force onto the cover part 18, such said upward facing surface portion 27 of the first member 16 is firmly and tightly engaged with a downward facing lower surface 29 of the cover part 18.

After the second member 20 has been integrally joined with at least the first member 16, the pressure pieces 30 may be retracted and removed. The upward pointing protrusions 22, 24 of the first member 16 are not only beneficial in terms of mutual assembly of cover part 18 and member 16 but also enlarge the total upper surface of the first member 16 in order to increase a bonding effect between first and second members 16, 20.

Depending on the type of material used for the first and second members 16, 20 mutual abutment and surface engaging bonding of selected surface portions of first member 16 and second member 20 may be sufficient to firmly fix the cover part 18 in the interface area 15. Additionally, it is conceivable, that the first member 16 comprises some kind of undercutting or indentations in upward facing surface portions so as to enable a positive interlock with the second injection molded member 20. It is also conceivable that the surface portions 26, 28 of the first member 16 to be brought in bonding contact with the second member 20 comprise a roughened or undulated surface structure. Additionally, it is also conceivable, that the second member 20 laterally embraces or laterally encloses also the lateral side edges 32 of the first member 16 in such a way, that the second member 20 even at least partially extends across the lower surface 17 of the first member.

Apart from the through opening left behind from the pressure pieces, the second member 20 preferably comprises a rather closed shape and structure and fills the entire space between the projections 22, 24 and an upward pointing upper face of the cover part 18. This way, the cover part 18 can be structurally and mechanically stabilized to seal the seals provide a sufficient seal of the channels 12, 14.

The fluid guiding assembly 10 as illustrated in FIG. 3 is of particular benefit when implemented in a medicament guiding assembly to be used in a drug delivery device. In detail, those portions of the first member 16 and the cover part 18 which directly enclose the channel structure 12, 14 do not have to be thermally treated in order to establish a liquid-tight seal of the channels 12, 14. Moreover, by means of the second member 20, the cover part 16 does not have to be directly bonded or otherwise interconnected with the first member. Those portions of first member 16 and second member 20 which are eventually thermally stressed or treated with heat are located outside the channel structures 12, 14. Preferably, the first member 16 and the cover part 18 which may get in direct contact with the medicament to be guided through the channel structure are made of the same material.

Thinking of a second or subsequent step of injection molding to create or to generate the second member 20 the cover part 18 may also provide a kind of thermally insulating functionality and may serve to thermally protect the channel structure 12, 14 arranged underneath the cover part 18.

Moreover it has to noted that the channel structure 12, 14 can be formed in the interface area 15 by a multiplicity of different ways. Mutually corresponding or complementing recessed structures or grooves of first member 16 and/or cover part 20 may be of rectangular, oval, circular shape. Also, a rather quadratic or rectangular channel structure may be formed by means of two mutually corresponding v-shaped grooves provided in the first member 16 and the cover part 18, respectively.

In accordance with the illustrated stages of assembly as shown in the sequence of FIGS. 1, 2 and 3, FIG. 4 is illustrative of a flowchart of subsequent method steps to be executed during manufacturing of the fluid guiding assembly. In a first step 100, the first member 16 is either created, e.g. by way of injection molding or is otherwise provided or supplied. Optionally and depending on the overall geometry of the first member 16, a groove or channel structure 12, 14 may be created, e.g. by way of any applicable ablation technique or by etching.

Thereafter, optional valves or other fluid flow manipulate elements which are not explicitly illustrated in the sketches of FIGS. 1 to 3 may be assembled and disposed in the channel structure 12, 14 in step 102. Subsequently, in step 104, a cover part 18 is arranged on top of the upward facing surface portion 27 of the first member 16 to seal and/or to close the channel structures 12, 14. Thereafter, in step 106, a pre-defined pressure is apply to the cover part 18 in order to press together cover part 18 and first member 16. This way, a liquid-tight sealing of the channel structures 12, 14 can be attained.

Thereafter or simultaneously to the pressure application, in a subsequent injection molding step 108, the second member 20 can be integrally joined with the first member, at least with surface portions 26, 28 of the first member 16 arranged outside the circumference or outside the area of the cover part 18. While cover part 18 and first member 16 are preferably made of FDA-compliant plastic material, the second member 20 may comprise a FDA-non-compliant plastic material. Also, the material the second member 20 is made of may exhibit a higher shrinkage rate compared to the material the first member 16 and/or cover part 18 is made of. When respective plastic materials become subject to shrinkage, e.g. during a cooling down after an injection molding process, different shrinkage rates may give rise to mechanical stress and mechanical tension across the interface of first and second members 16, 20, thereby increasing a sealing pressure on the cover part 18.

The material of the second member 20 may feature a lower or different melting point compared to the material the first member 16 or the cover part 18 is or are made of. Hence, during the second or final injection molding process, the first member 16 and the cover part 18 may only become subject to a comparatively low degree of thermal stress.

Generally, the first and the second member may also be made of the same injection moldable plastic material.

Figure 5:
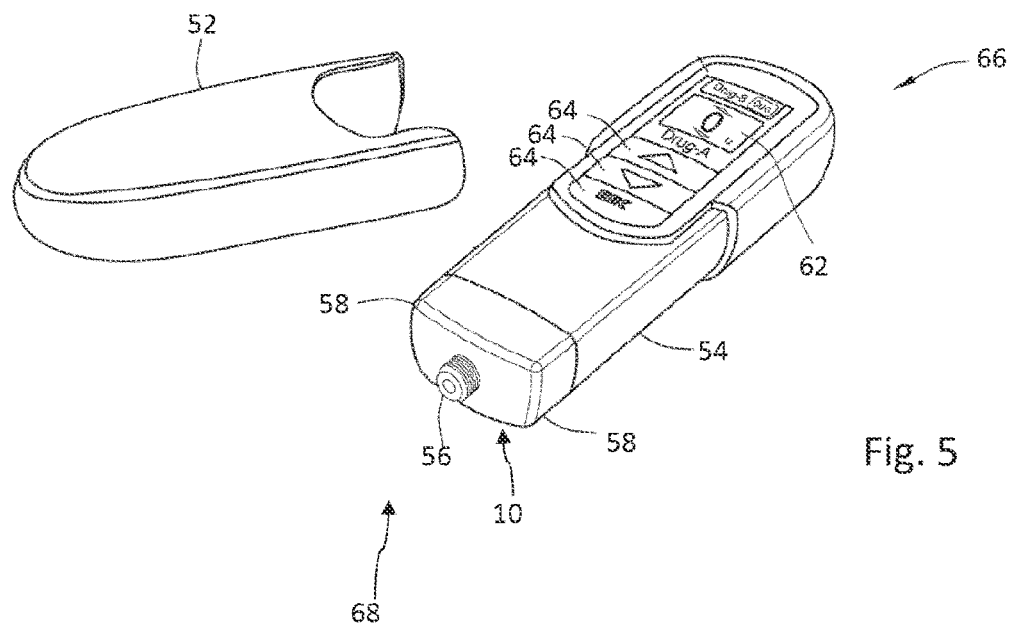
FIG. 5 shows one of a plurality of conceivable drug delivery devices making use of the fluid guiding assembly in a perspective view.
Figure 6:
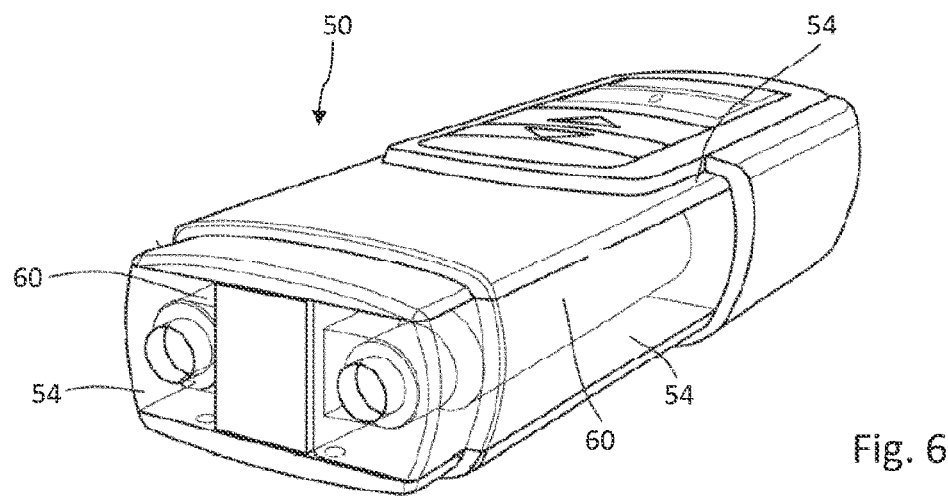
FIG. 6 shows the device according to FIG. 5 in a partially transparent illustration.

FIG. 5 is finally indicative of a hand-held drug delivery device 50 having a housing 54 and a removable cap 52. The device 50 comprises a dispensing end 56 near a distal end section 68 which is designed as threaded socket e.g. in order to threadedly receive a needle hub having e.g. a double-tipped injection needle in order to dispense a medicament by way of injection. As further illustrated in FIG. 6, the housing 54 accommodates two cartridges 60 at least partially filed with a medicament. Additionally, the device 50 as shown in FIG. 5 comprises an interface 58 to provide fluid communication between the dispensing end 56 and with any one of said cartridges 60. The interface 58 of FIG. 5 may be equipped with a fluid guiding assembly 10 as illustrated in FIGS. 1 to 3 in order to provide mixing of medicaments provided in the two cartridges 60 or to provide sequential dispensing of different medicaments via the single dispensing end 56.

As further illustrated in FIG. 5, the device comprises a display element 62 near its proximal end 66 as well as a variety of buttons or key elements 64 to control and/or to manipulate the medicament dispensing action.

The invention claimed is:

1. A drug delivery device adapted to dispense a predefined amount of a medicament via an outlet, comprising:
   a housing to receive at least one cartridge at least partially filled with a medicament,
   a dispensing end to dispense a predefined amount of the medicament, and
   a fluid guiding assembly disposed between the cartridge and the dispensing end, wherein the fluid guiding assembly comprises:
   a first member,
   a cover part adjacently disposed to the first member and being in non-bonded surface contact with a surface portion of the first member thereby forming an interface area, wherein the interface area is defined by surface portions of the first member and the cover part that are in direct contact with each other,
   at least one channel structure located in the interface area and extending along the interface area of first member and cover part and being formed by at least one recess in either the first member and/or in the cover part,
   wherein the at least one channel structure of the fluid guiding assembly is arranged in a fluid path between the cartridge and the dispensing end, and
   a second injection molded member being in contact with the cover part and being bonded to the first member by way of injection molding to fix the cover part relative to the first member and wherein there is provided a substance-to-substance bonding between the first and the second member.

2. The drug delivery device according to claim 1, wherein the first member comprises an injection molded plastic component.

3. The drug delivery device according to claim 1, wherein the second member comprises an injection molded plastic component.

4. The drug delivery device according to claim 1, wherein the cover part and/or the first member comprise an inert plastic material.

5. The drug delivery device according to claim 1, wherein first and second members are mutually interconnected in regions outside the cover part.

6. The drug delivery device according to claim 1, wherein the second member and/or the first member at least partially enclose the cover part.

7. The drug delivery device according claim 1, wherein the interface between cover part and first member is substantially liquid-tight.

8. The drug delivery device according to claim 1, wherein the guiding assembly is designed as a needle hub or as a cartridge hub of the drug delivery device.

9. The drug delivery device according to claim 1, wherein the first member comprises an undercutting or indentation in a surface portion that is in bonding contact with the second member.

10. The drug delivery device according to claim 1, wherein the second member laterally embraces or laterally encloses a lateral side edges of the first member and wherein the second member at least partially extends across a lower surface of the first member facing away from the cover part.

11. The drug delivery device according to claim 1, wherein the material the second member is made of exhibits a higher shrinkage rate compared to the material the first member or the cover part is made of.

12. A method of manufacturing a drug delivery device according to claim 1, comprising the steps of:
   providing a first member,
   arranging a cover part adjacent to the first member to form an interface area in which first member and cover part get in direct contact with each other, wherein the cover part and/or the first member comprise at least one recess extending along the interface area to form a channel structure,
   engaging the first member with a second member at least being in contact with the cover part to fix the same relative to the first member, and
   bonding the second member to the first member by way of injection molding after first member and cover part have been mutually assembled.

13. The method according to claim 12, wherein the first member and/or the cover part are injection molded and comprise at least one recess extending across an interface forming surface portion.

14. The method according to claim 12, wherein the cover part is sealingly pressed against the first member during injection molding of the second member.

* * * * *